US00PP23367P2

(12) United States Plant Patent
Blom

(10) Patent No.: US PP23,367 P2
(45) Date of Patent: Jan. 29, 2013

(54) ***CHRYSANTHEMUM* PLANT NAMED 'ZANMUFLAMINCRAN'**

(50) Latin Name: *Chrysanthemum×morifolium* Ramat.
Varietal Denomination: Zanmuflamincran

(75) Inventor: Wilhelmus Bernardus Blom, Leimuiden (NL)

(73) Assignee: Chrysanthemum Breeders Association Research B.V., Valkenburg Z-H (NL)

( * ) Notice: Subject to any disclaimer, the term of this patent is extended or adjusted under 35 U.S.C. 154(b) by 0 days.

(21) Appl. No.: 13/200,324

(22) Filed: Sep. 23, 2011

(51) Int. Cl.
*A01H 5/00* (2006.01)

(52) U.S. Cl. ..... Plt./298

(58) Field of Classification Search ..... Plt./298
See application file for complete search history.

*Primary Examiner* — Annette Para

(74) *Attorney, Agent, or Firm* — Steptoe & Johnson LLP

(57) ABSTRACT

A *Crysanthemum* plant named 'Zanmuflamincran' characterized by its medium sized blooms with red-purple ray florets and prolific branching; natural season flower date September 6 (week 36) ; blooming for a period of 5 weeks.

3 Drawing Sheets

Botanical designation: *Chrysanthemum×morifolium* Ramat.

Cultivar denomination: 'Zanmuflamincran'.

RELATED CULTIVARS

The new plant is related to 'Zanmuflamin' (U.S. Plant Pat. No. 20,589). The new cultivar is a mutant of 'Zanmuflamin'.

BACKGROUND OF THE INVENTION

The present invention relates to a new and distinct cultivar of *Chrysanthemum* plant, botanically known as *Chrysanthemum×morifolium* Ramat., commercially known as a garden mum, and hereinafter referred to by the cultivar denomination 'Zanmuflamincran'. The new plant is a product of a breeding and selection program which had the objective of finding color mutants from existing parent plants. The new plant comprises a whole plant mutant of the parent *Chrysanthemum* named 'Zanmuflamin'. Plants from the new cultivar 'Zanmuflamincran' differ from plants of the female parent in the color of the ray-florets. The color is red-purple in the mutant, while it is purple in the parent.

The new cultivar was discovered as a color mutant in September 2006 by Wilhelmus Bemardus Blom in a controlled environment (greenhouse) in Rijsenhout, The Netherlands. The first act of asexual reproduction of 'Zanmuflamincran' was accomplished when after planting of the mutant as a motherplant in Rijsenhout; vegetative cuttings from this mutant were taken and propagated further. The new cultivar has been found to retain its distinctive characteristics through successive propagations.

BRIEF DESCRIPTION OF THE DRAWINGS

The present invention of a new and distinct variety of *Chrysanthemum* is shown in the accompanying drawings, the color being as nearly true as possible with color photographs of this type.

DESCRIPTION OF THE INVENTION

Figure 1:
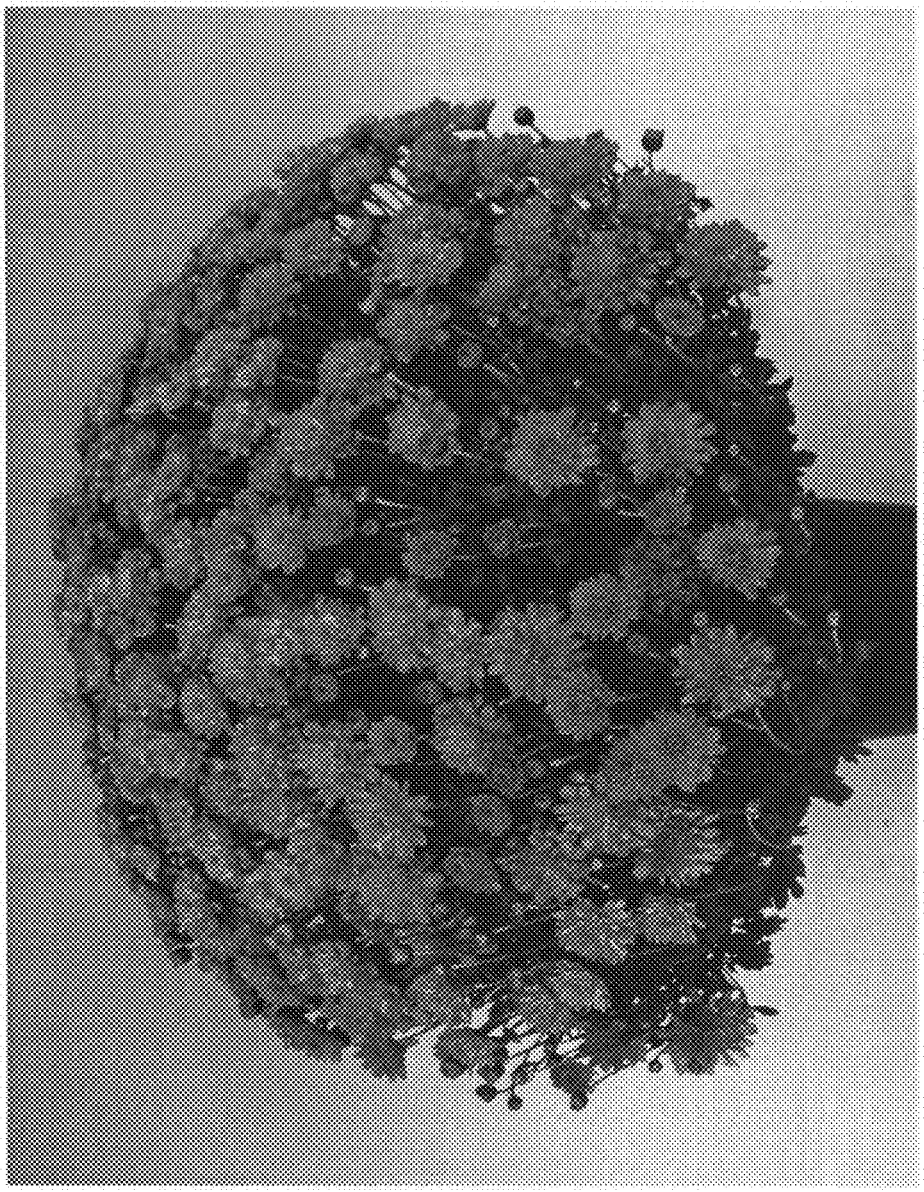
FIG. 1 shows a plant of the cultivar in full bloom.
Figure 2:
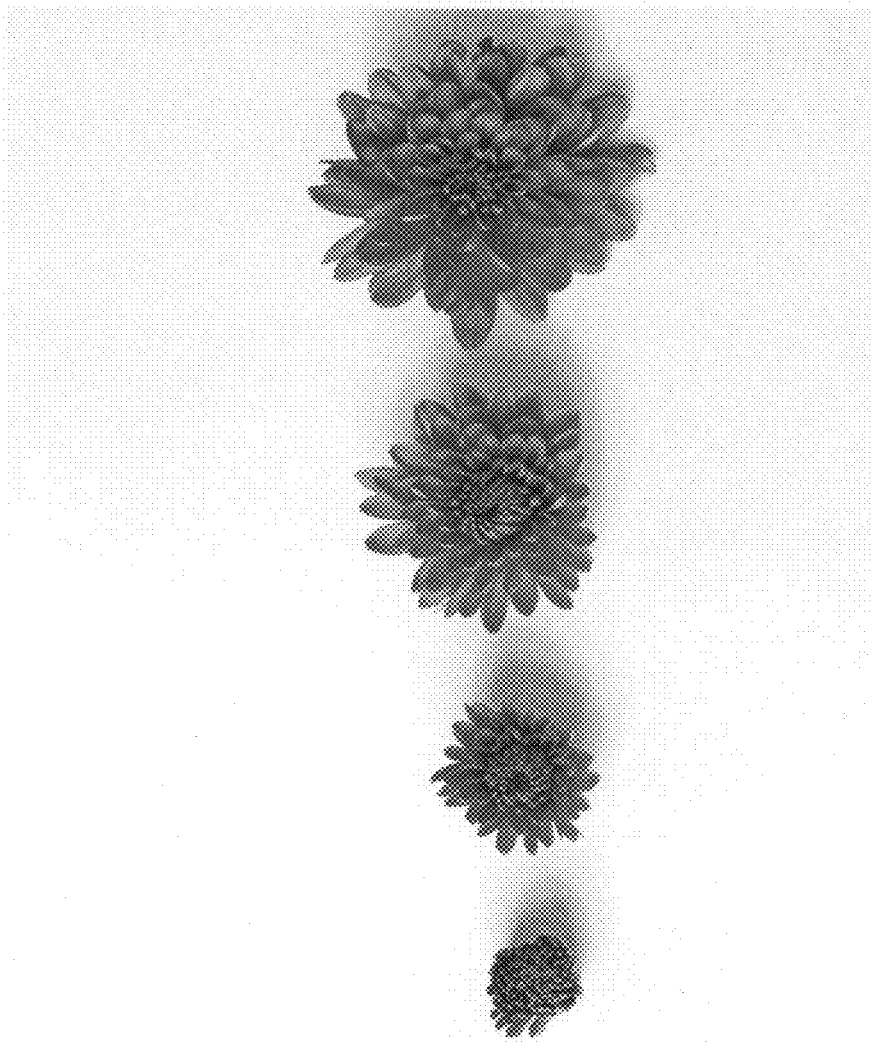
FIG. 2 shows the various stages of blooms of the new cultivar.
Figure 3:
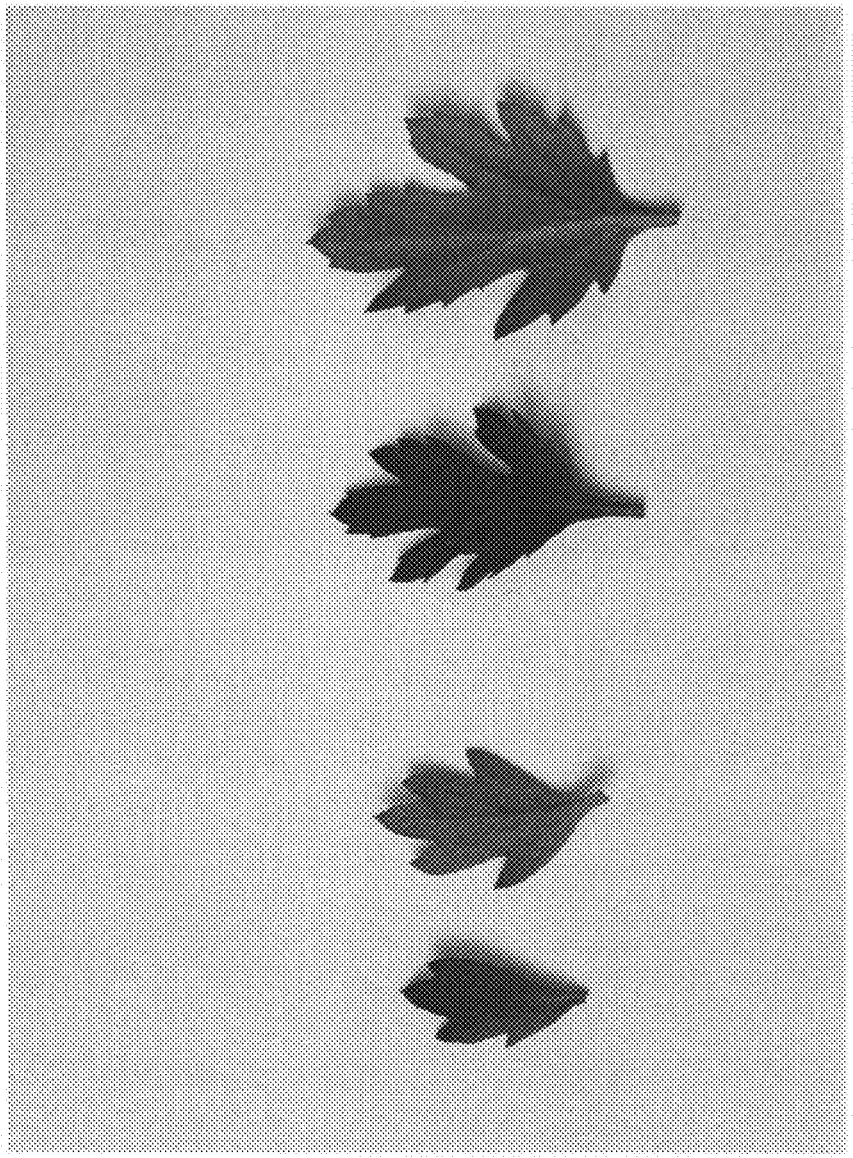
FIG. 3 shows the various stages of foliage of the new cultivar.

The observations and measurements were gathered from plants grown out door in Rijsenhout, The Netherlands, under natural day length and temperature and planted in week 23 in 2010. The natural blooming date of this crop was September (week 36). The average height of the plants was 35 cm. No gowth retardants were used. No tests were done on disease or insects resistance or susceptibility. No tests were done on cold or drought resistance. This new variety produces medium sized blooms with red-purple ray florets blooming for a period of 5 weeks.

From the cultivars known to inventor the most similar existing cultivar in comparison to 'Zanmuflamincran' are its parent 'Zanmuflamin' (U.S. Plant Pat. No. 20,589), and another colour mutant 'Zanmuflaminpine', developed from the same parent (U.S. Plant Patent Application Pending) . When 'Zanmuflamin' and 'Zanmuflamincran', 'Zanmuflaminpine' are being compared the following difference is noticed: The ray florets of 'Zanmuflamin' are purple colored, while those of 'Zanmuflamincran' are red-purple and those of 'Zanmuflaminpine' are salmon colored.

The following is a description of the plant and characteristics that distinguish 'Zanmuflamincran' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour chart, edition 2001.

TABLE 1

| Detailed Botanical Description | |
|---|---|
| Bud | |
| Size | Small; cross-section 6 mm, height 4 mm |
| Shape | Round |
| Texture | Pubescent |
| Outside Color | Greyed-green 191A |

TABLE 1-continued

| Detailed Botanical Description | |
|---|---|
| Phyllaries | |
| Number | 22, arranged in 3 rows |
| Shape | Elliptic |
| Apex | Acute |
| Base | Truncate |
| Margin | Entire |
| Color | Upper surface: Green N 138B<br>Lower surface: Green N138C |
| Length and width | 4 mm; 2 mm |
| Texture | Pubescent |
| Inflorescences | |
| Type | Double |
| Height | 2 cm |
| Diameter | 4.5-5 cm |
| Peduncle length | 9-10 cm |
| Peduncle color | Yellow-green 146C |
| Peduncle diameter | 2 mm |
| Peduncle texture | Pubescent |
| Number per branch | Approx. 7 inflorescences |
| Duration of flowering | 5 weeks |
| Seeds | Produced in small quantities, ovate, Greyed-brown 199A, length 1.5 mm, diameter 0.5 mm |
| Fragrance | Faint chrysanthemum odor |
| Color | |
| Center of inflorescence | Immature stage: Greyed-purple 183B<br>Mature stage: Yellow-green 150C |
| Color of upper surface of the ray-florets | Yellow 6B at base to Red 47A at apex |
| Color of the lower surface of the ray-florets | Yellow 6C at base to Greyed-Red 182B at apex |
| Tonality from Distance | A garden mum with red-purple blooms |
| Color of the ray-florets after aging of the plant | Greyed-purple 186D |
| Ray florets | |
| Texture | Upper and lower surface smooth |
| Number | 190-210 |
| Shape | Elliptic |
| Apex | Rounded to dentate |
| Base | Attenuate |
| Cross-section | Flat to convex |
| Longitudinal axis of majority | Straight |
| Length of corolla tube | 4 mm |
| Ray-floret margin | Entire |
| Ray-floret length | 1.5-2.3 cm |
| Ray-floret width | 3.5-5 mm |
| Ratio length/width | High |
| Disc florets | Absent |
| Receptacle | |
| Color | Yellow-green 145D |
| Shape | Domed raised |
| Height | 5 mm |
| Diameter | 4 mm |
| Reproductive Organs | |
| Androecium | Absent |
| Gynoecium | Present in ray florets |
| Style color | Yellow-green 154C |
| Style Length | 3 mm |

TABLE 1-continued

| Detailed Botanical Description | |
|---|---|
| Stigma color | Yellow 7A |
| Stigma Width | 1 mm |
| Ovary | Enclosed in calyx |
| Plant | |
| Form | Grown as a spray type pot mum, outdoor raised and mounded |
| Growth habit | Spherical shape |
| Growth rate | Medium to high |
| Height | 35 cm |
| Width | 55 cm |
| Stem Color | Greyed-brown 199A |
| Stem Strength | Strong |
| Stem Brittleness | Not brittle |
| Stem Anthocyanin Coloration | Greyed-purple 185C |
| Internode length | 2-3 cm |
| Length of lateral branch | From top to bottom 20-22 cm |
| Lateral branch color | Green 137 C |
| Lateral branch, attachment | Strong |
| Lateral branch diameter | 2 mm |
| Branching (average number of lateral branches) | Prolific with 8 breaks after pinching |
| Natural season blooming date | September 6 (week 36) |
| Foliage | |
| Leaf color | Upper side: Green N138B<br>Lower side: Green 138C |
| Color midvein | Upper side: Yellow-green 147D<br>Lower side: Yellow-green 148D |
| Size | Small; length 3-5cm, width 2-3 cm |
| Quantity (number per lateral branch) | 18-20 |
| Shape | Elliptic |
| Texture upper side | Sparsely pubescent |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Attenuate to truncate |
| Apex | Mucronulate |
| Petiole length | 1-2 cm |
| Petiole diameter | 2 mm |
| Petiole color | Yellow-green 147D |

TABLE 2

| Differences with the comparison varieties | | | |
|---|---|---|---|
| | 'Zanmuflamincran' | 'Zanmuflaminpine' | 'Zanmuflamin' |
| Color upper-surface ray florets | Yellow 6B at base to Red 47A at most part | Yellow-white 158B at base to Greyed-purple 186C at most part | Red-Purple58A |

I claim:

1. A new and distinct *Chrysanthemum* plant named 'Zanmuflamincran' as described and illustrated.

* * * * *